United States Patent [19]

Scalese

[11] Patent Number: 4,629,984

[45] Date of Patent: Dec. 16, 1986

[54] FERROMAGNETIC EDDY CURRENT PROBE APPARATUS

[76] Inventor: Joseph J. Scalese, 5531 Laird Rd., Loomis, Calif. 95650

[21] Appl. No.: 705,835

[22] Filed: Feb. 26, 1985

[51] Int. Cl.$^4$ ...................... G01N 27/72; G01R 33/12
[52] U.S. Cl. ................................ 324/228; 336/84 M; 324/219; 324/234
[58] Field of Search ............... 324/219, 220, 227, 228, 324/236, 237, 238, 239, 240, 262, 234; 336/84 M, 84 R, 84 C

[56] References Cited

U.S. PATENT DOCUMENTS

| | | | |
|---|---|---|---|
| 3,555,412 | 1/1971 | Fowler | 324/37 |
| 3,718,855 | 2/1973 | Rogel et al. | 324/234 X |
| 3,831,084 | 8/1974 | Scalese et al. | 324/40 |
| 4,204,159 | 5/1980 | Sarian et al. | 324/232 |
| 4,219,774 | 8/1980 | Rogel et al. | 324/262 |
| 4,441,078 | 4/1984 | Lecomte | 324/219 |
| 4,454,473 | 6/1984 | Rosauer | 324/262 |

Primary Examiner—Reinhard J. Eisenzopf
Assistant Examiner—Robert W. Mueller
Attorney, Agent, or Firm—William Stepanishen; Donald J. Singer

[57] ABSTRACT

A ferromagnetic eddy current probe apparatus having a double shielded magnetic coil to reduce the size of the magnetic filed and to generate a sharply focused electromagnetic field. A ferromagnetic steel alloy provides a double shield effect for greater concentration of the electromagnetic field onto a test specimen, and also to prevent probe tip wear and deformation when used to inspect fastener holes with a high speed designed feature maintenance the size setting of the probe (coil-end) diameter. An expansion slot in the end of the probe provides a spring action during probe radiation to keep a constant contact with the wall of a fastener hole. The ferromagnetic probe portion is removeable from the shank-end (a non-metallic portion of the probe) for easy repair or replacement and provides electrical isolation to prevent shorting of the signal.

8 Claims, 4 Drawing Figures

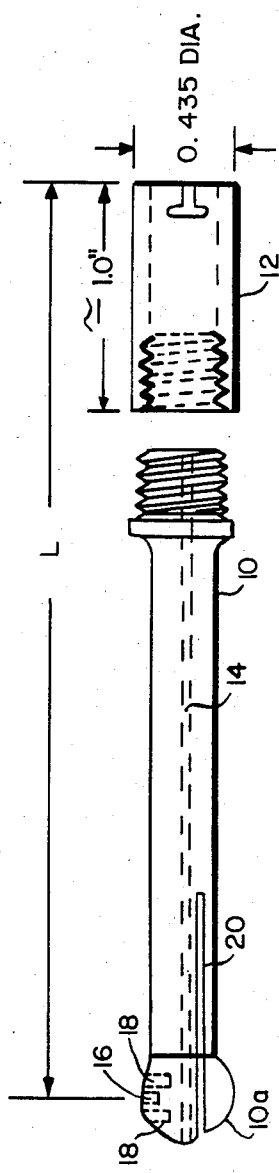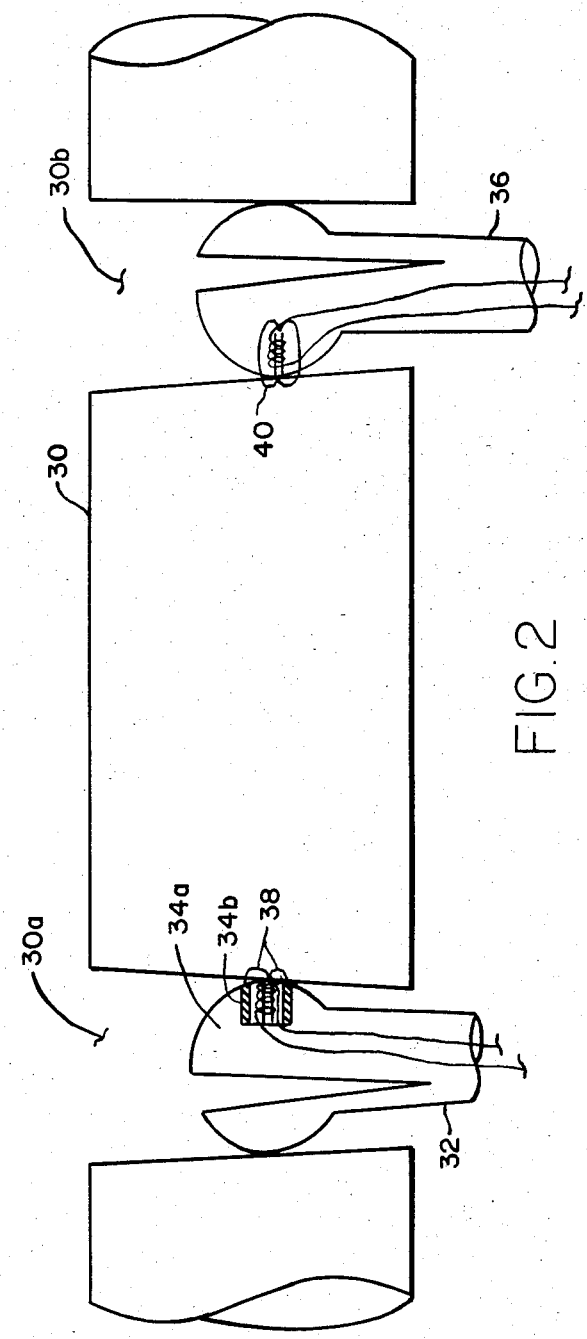
FIG.1
FIG.2

FERROMAGNETIC EDDY CURRENT PROBE APPARATUS

STATEMENT OF GOVERNMENT INTEREST

The invention described herein may be manufactured and used by or for the Government for governmental purposes without the payment of any royalty thereon.

BACKGROUND OF THE INVENTION

The present invention relates broadly to an eddy current probe apparatus, and in particular to a ferromagnetic eddy current probe apparatus.

Nondestructive test methods are used to inspect the structural integrity of critical structural members, particularly in aircraft. Eddy current testing has proved to be invaluable in detecting metal flaws in fastener holes when the cracks are minute-size, less than 0.010 inch in depth, and 0.010 inches long axially. At present, it is the only practical method for reliably detecting small, tight cracks with a minimum of hole and surface preparation prior to testing. Eddy current techniques require the use of probes to initiate eddy currents into a test specimen or structural member. This is accomplished through the use of eddy current probe in which an alternating current at a suitable frequency is applied to a test coil that is located at the probe tip. The magnetic field in the test coil induces eddy currents into the structural part which is in contact with or in close proximity to the eddy current probe.

Prior to the development of automatic eddy current scanning at McClellan AFB by this inventor, the standard eddy current technique for detecting fatigue cracks in fastener holes was the hand-scanning method. This involved rotating a hand-held eddy current probe 360 degrees by hand thru a fastener hole while an inspector observed needle movement of the eddy current instrument. Due to the many negative factors associated with performing hand inspection in general, and the difficulty of hand-probe inspection of fastener holes in particular, more than 200 Automatic Eddy Current Flaw Detector Systems are in use by Air Force NDI personnel today.

The present invention relates to a special fastener hole probe with increased sensitivity which cannot become deformed while rotating at any speed. The present probes which are made of nylon or Delrin can become deformed when operated in an automatic detection system that rotates the test probe. Therefore, it may be seen that the new special probe greatly improves the reliability of the Automatic Eddy Current Flaw Detection Systems which is in use throughout the Air Force.

SUMMARY OF THE INVENTION

The present invention utilizes a ferromagnetic eddy current probe apparatus which detects flaws and cracks in structural parts, such as fastener holes while being rotated at high scanning speeds. The use of ferromagnetic steel for the probe tip provides a double shield effect which increase sensitivity and reduces noise. The end of the probe includes an expansion slot which provides a spring action to maintain a constant contact with the wall of the fastener hole under test.

It is one object of the present invention, therefore, to provide an improved ferromagnetic eddy current probe apparatus.

It is another object of the invention to provide an improved ferromagnetic eddy current probe apparatus which can inspect holes at a rate five times faster than conventional probes.

It is another object of the invention to provide an improved ferromagnetic eddy current probe apparatus which has greater sensitivity and reduced noise due to its double shielded construction.

It is another object of the invention to provide an improved ferromagnetic eddy current probe apparatus which will cut the cost of probe replacements due to wear and damage since it is more durable and is repairable.

It is another object of the invention to provide an improved ferromagnetic eddy current probe apparatus which maintains inspection sensitivity at high-speed scanning due to constant wall cantact.

It is another object of the invention to provide an improved ferromagnetic eddy current probe apparatus which will cut time in man-hours per aircraft when it is required to evaluate hundreds of fastener holes for the presence of cracks.

It is another object of the invention to provide an improved ferromagnetic eddy current probe apparatus which permits a high degree of confidence in inspection results due to the well defined signal track produced by this probe.

These and other advantages, objects and features of the invention will become more apparent after considering the following description taken in conjunction with the illustrative embodiment in the accompanying drawings.

BRIEF DESCRIPTION OF THE DRAWINGS

FIG. 1 is a side view of the ferromagnetic eddy current probe apparatus according to the present invention;

FIG. 2 is a plan view of the eddy current fields of a double-shielded probe versus an unshielded probe;

DESCRIPTION OF THE PREFERRED EMBODIMENT

Figure 3:
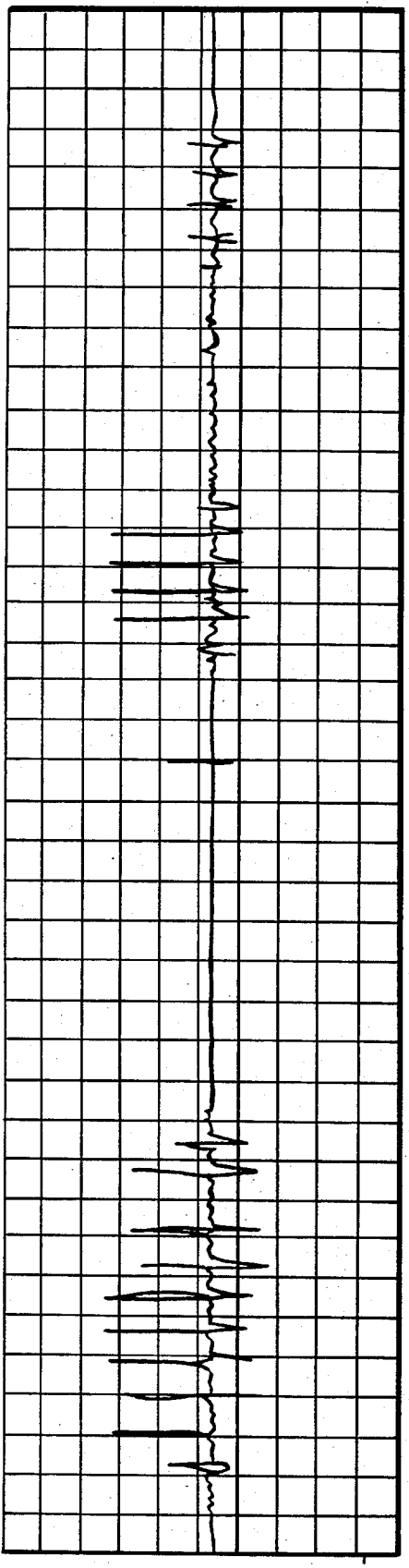
FIG. 3 is a graphic representation of the detected flaw indications using the ferrmagnetic eddy current probe apparatus.

Referring now to FIG. 1, there is shown a ferromagnetic eddy current probe apparatus comprising a first and second probe portions 10, 12. The mating ends of the first and second probe portions 10, 12 are respectively threaded to facilitate assembly into a single eddy current probe for flaw detection operation. The assembled length of the probe as indicated by L is approximately 2.64 inches. A coil lead hole 14 extends through the center portion of the first probe portion 10 to permit the insertion and connection of the coil lead wire (not shown) with the coil 16 and magnetic field generation source (not shown). A shield 18 which is comprised of ferrite or any other suitable metal material, is provided to substantially surround the core and coil 16 and direct its magnetic field in a direction that is substantially perpendicular to the central axis of the first probe portion 10. The tip 10a of the first probe portion 10 is substantially spherical and includes an expansion slot 20 has a thickness of approximately 0.020 inches. While the first probe portion 10 is comprised of a ferromagnetic steel alloy which in combination with the shield 18 provides a double shield for coil 16, the second probe portion 12 is comprised of plastic, phenolic or any other suitable non-metal material with the necessary strength and machining properties. The non-metal second probe portion 12 provides electrical isolation for the overall eddy current probe.

The ferromagnetic probe apparatus illustrates an eddy current probe that performs extremely well at high-speed while scanning in fastener holes in an automatic test apparatus such as the previously described automatic eddy current scanning flaw detector system. It can be used without becoming deformed or worn while rotating at high speed due to the alloy steel body. This probe can be disassembled and repaired thereby offering a considerable savings in replacement cost since new high-speed probes are expensive. It cannot shortout due to the non-metallic shank design. The ferromagnetic eddy current probe apparatus has greater sensitivity, because it is made of ferromagnetic steel in combination with shield 18 provides a double shield effect and thereby reduces noise. Commercially available probes are made of nylon or Delrin. The ferromagnetic steel probe includes an expansion slot 20 which maintains the size setting of the probe (coil-end) diameter. The expansion slot 20 in the end of the probe acts in a manner similar to a spring to keep a constant contact to the hole wall of the test specimen. While the probe is rotating at high-speed this end of the probe can become compressed if it were made of conventional probe materials. It would no longer stay in contact to the material being tested, nor could it produce valid test results. Quite to the contrary, the ferromagnetic steel probe apparatus offers retention to a expansion condition (snug fit during rotation) for better tension of the coil-end against the wall of the hole being tested. It will also be noted that the constant probe contact with the test specimen reduces signal noise from vibration and bounce due to having less rotational drag.

Turning now to FIG. 2, there is shown a test specimen 30 with a pair of test holes 30a, 30b. The ferromagnetic steel probe 32 with its double shield 34a, 34b is shown position in test hole 30a which is tapered. In test hole 30b which is also tapered there is shown a conventional unshielded probe 36 which is made of nylon or other similar type material. It may be noted that the magnetic field 38 of the ferromagnetic steel probe 32 is more sharply defined and concentrated into the test specimen 30 as compared to the magnetic field of the conventional nylon probe 36 which is spread over a larger area.

Figure 4:
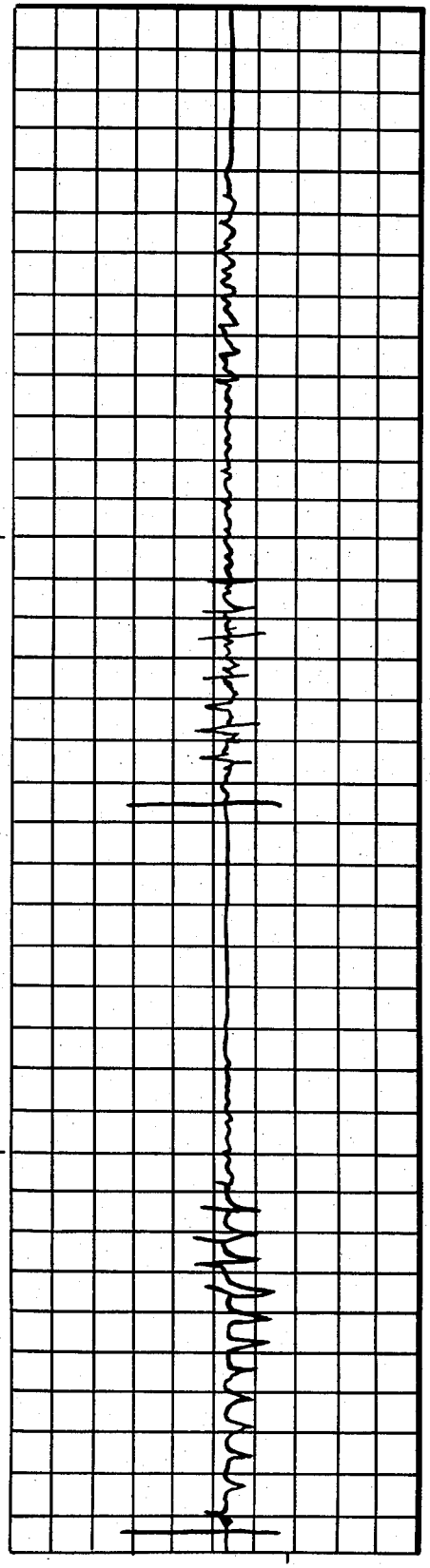
FIG. 4 is a graphic representation of the detected flaw indications using a conventional probe.

The use of ferromagnetic steel for the eddy current probe body provides the added benefit that comes from having a double shield effect. Due to the nature of the magnetic field around the coil of an unshielded eddy current probe, the magnetic field often spread over and affects an area larger than is desired. This larger area of magnetic field concentration permits unwanted noise signals to pass along with crack signals into the detection equipment, thus making a recording trace difficult to evaluate. This effect is clearly shown by a comparison of the signal recording shown in FIGS. 3 and 4 respectively. In FIG. 3, the recording was made with automatic scanning at 500 RPM using the ferromagnetic steel probe. At the left is a trace of the calibration standard. The first flaw indication shows a defect size of approximately 0.020 inch depth by 0.100 inch length, the second defect at the left is approximately 0.005" depth by 0.050 length. In FIG. 4, the recording was made of the same aircraft specimen with a conventional probe. It should be noted that the noise on the base line makes it difficult to evaluate the flaw indications. Thus, the additional benefit that comes from the ferromagnetic steel probe with the extra shield effect is clearly illustrated by the traces in FIGS. 3 and 4. The ferromagnetic steel body probe plus the ferrite shield around the coil causes the magnetic field induced into a test specimen to be highly concentrated. Thus, the focus on the area being tested becomes very small because of the use of a double shield around the magnetic test coil. The use of the double shield results in greater sensitivity, less noise and sharper crack indications. The problem of having to resolve unwanted noise is substantially eliminated when the ferromagnetic steel probe is utilized for flaw detection.

Although the invention has been described with reference to a particular embodiment, it will be understood to those skilled in the art that the invention is capable of a variety of alternative embodiments within the spirit and scope of the appended claims.

What is claimed is:

1. A ferromagnetic eddy current probe apparatus comprising in combination:

a first probe means comprised of a metal material, said first probe means having a spherical portion at one end and a externally threaded portion at the other end, said first probe means containing a hole extending along its central axis, said spherical portion of said first probe means containing a shallow opening which communicates with said hole, said shallow opening enclosed by walls that are formed in said metal material of said first probe means, a magnetic coil means is positioned within said shallow opening, said magnetic coil means is surrounded by a shield means which is positioned between said magnetic coil means and the walls of said shallow opening, said magnetic coil means including coil lead wires which extend into said hole and exit at said thread portion of said first probe means, said first probe means including an expansion slot extending longitudinally through said spherical portion, said shallow opening is extended to communicate with said expansion slot of said first probe means in order to increase probe sensitivity, said expansion slot having a predetermined thickness, and, a second probe means comprised of a non-metallic material, said second probe means having an internally threaded portion at one end to mate with said externally threaded portion of said first probe means, said second probe means accepting said coil lead wires to provide access to an excitation means.

2. A ferromagnetic eddy current probe apparatus as described in claim 1 wherein said metallic material of said first probe means comprises ferromagnetic steel alloy.

3. A ferromagnetic eddy current probe apparatus as described in claim 2 wherein said second probe means provides electrical isolation for said first probe means.

4. A ferromagnetic eddy current probe apparatus as described in claim 2 wherein said predetermined thickness of said expansion slot is 0.020 inches.

5. A ferromagnetic eddy current probe apparatus as described in claim 2 wherein said shield means is comprised of a magnetic-conducting metal.

6. A ferromagnetic eddy current probe apparatus as described in claim 2 wherein said shield means is comprised of ferrite.

7. A ferromagnetic eddy current probe apparatus as described in claim 2 wherein said ferromagnetic steel of said first probe means in combination with said shield means provides a double shield for the magnetic field which is generated by said magnetic coil means.

8. A ferromagnetic eddy current probe apparatus as described in claim 2 wherein said magnetic field is highly concentrated into a small area.

* * * * *